United States Patent
Burdea et al.

(10) Patent No.: US 9,522,316 B2
(45) Date of Patent: Dec. 20, 2016

(54) INSTRUMENTED THERAPY TABLE AND SYSTEM

(75) Inventors: Grigore C. Burdea, Highland Park, NJ (US); Bryan A. Rabin, North Brunswick, NJ (US); Doru T. Roll, Long Beach, NY (US)

(73) Assignee: Bright Cloud International Corp., Highland Park, NJ (US)

( * ) Notice: Subject to any disclaimer, the term of this patent is extended or adjusted under 35 U.S.C. 154(b) by 1674 days.

(21) Appl. No.: 13/026,197

(22) Filed: Feb. 11, 2011

(65) Prior Publication Data

US 2011/0257566 A1  Oct. 20, 2011

Related U.S. Application Data

(60) Provisional application No. 61/304,319, filed on Feb. 12, 2010.

(51) Int. Cl.
*A63B 71/00* (2006.01)
*A63B 21/00* (2006.01)
(Continued)

(52) U.S. Cl.
CPC ......... *A63B 71/0009* (2013.01); *A63B 21/068* (2013.01); *A63B 21/4017* (2015.10); *A63B 21/4021* (2015.10); *A63B 24/0006* (2013.01); *A63B 24/0075* (2013.01); *A63B 71/0622* (2013.01); *G06F 19/3481* (2013.01);
(Continued)

(58) Field of Classification Search
CPC ............... A61H 2201/1657; A61H 2201/1659; A61H 2201/5061; A61H 2201/5066; A61H 2201/1638; A61H 1/0285; A61B 5/7475; G06F 19/3481; G06F 3/0482; G06F 1/109; G06F 3/0412; G06F 1/1626
See application file for complete search history.

(56) References Cited

U.S. PATENT DOCUMENTS 4,885,687 A * 12/1989 Carey .................... A61B 5/225 273/440
5,241,952 A * 9/1993 Ortiz .................... A63B 23/12 434/261

(Continued)

*Primary Examiner* — Sundhara Ganesan
(74) *Attorney, Agent, or Firm* — Chiesa Shahinian & Giantomasi PC

(57) ABSTRACT

A modular, instrumented rehabilitation table and method of rehabilitation are disclosed. The table top can have a low friction top, a high friction bottom, a hollow section and no legs. An electronic controller is embedded in the hollow section of the table top. A first tilt sensor is embedded in the hollow section of the table top so as to sense tilt on a first axis. A second tilt sensor is embedded in the hollow section of the table top so as to sense tilt on a second axis. A tracking circuit, which can include a plurality of sensors arranged in a matrix format is provided. These can be embedded in the hollow section of the table top or can be atop the top surface of the table. A power supply embedded in the hollow section of the table top is provided. A communication circuit attached to the table top and electrically connected to the electronic controller is provided. The electronic controller sends a transmission signal including signals from the first tilt sensor, the second tilt sensor and the tracking circuit to the communication circuit which transmits the transmission signal.

11 Claims, 16 Drawing Sheets

(51) Int. Cl.
 *A63B 71/06* (2006.01)
 *A63B 24/00* (2006.01)
 *A63B 21/068* (2006.01)
 *G06F 19/00* (2011.01)
 *A63B 71/02* (2006.01)

(52) U.S. Cl.
 CPC ... *A63B 21/4005* (2015.10); *A63B 2071/0018* (2013.01); *A63B 2071/0081* (2013.01); *A63B 2071/025* (2013.01); *A63B 2209/08* (2013.01); *A63B 2209/10* (2013.01); *A63B 2220/24* (2013.01); *A63B 2220/56* (2013.01); *A63B 2220/801* (2013.01); *A63B 2220/805* (2013.01); *A63B 2220/806* (2013.01); *A63B 2225/20* (2013.01); *A63B 2225/50* (2013.01)

(56) References Cited

U.S. PATENT DOCUMENTS

| | | | | |
|---|---|---|---|---|
| 5,562,104 | A * | 10/1996 | Hochberg | A61B 5/4082 600/595 |
| 5,755,576 | A * | 5/1998 | Dunn | A61B 5/162 273/454 |
| 5,772,611 | A * | 6/1998 | Hocherman | A61B 5/1101 600/595 |
| 6,082,545 | A * | 7/2000 | Ford | A45C 3/02 206/315.1 |
| 6,162,189 | A * | 12/2000 | Girone | A61B 5/1036 482/79 |
| 6,613,000 | B1 * | 9/2003 | Reinkensmeyer | A61B 5/221 600/587 |
| 7,618,381 | B2 * | 11/2009 | Krebs | A61H 1/0285 601/5 |
| 7,725,175 | B2 * | 5/2010 | Koeneman | A61H 1/02 600/546 |
| 9,028,258 | B2 | 5/2015 | Burdea | |
| 2003/0231189 | A1 * | 12/2003 | Williams | G06F 1/1626 345/659 |
| 2006/0079817 | A1 * | 4/2006 | Dewald | A61H 1/02 601/5 |
| 2007/0219049 | A1 * | 9/2007 | Sheeks | A63B 21/15 482/1 |
| 2007/0282228 | A1 * | 12/2007 | Einav | A61B 5/7475 601/33 |
| 2008/0123287 | A1 * | 5/2008 | Rossell | G06F 1/1632 361/679.3 |
| 2009/0131225 | A1 * | 5/2009 | Burdea | A63B 21/06 482/5 |
| 2010/0179453 | A1 * | 7/2010 | Schweighofer | A61B 5/1118 600/595 |
| 2011/0025265 | A1 * | 2/2011 | Mochida | G06K 19/0701 320/108 |
| 2011/0112441 | A1 * | 5/2011 | Burdea | A63B 21/06 600/595 |
| 2011/0224583 | A1 * | 9/2011 | Lequeux | A61H 1/0237 601/5 |
| 2011/0237400 | A1 * | 9/2011 | King | A61H 1/0274 482/8 |
| 2011/0295165 | A1 * | 12/2011 | Cavallaro | A61H 1/0274 601/33 |

* cited by examiner

INSTRUMENTED THERAPY TABLE AND SYSTEM

STATEMENT OF RELATED CASES

This application claims the benefit of U.S. Provisional Application Ser. No. 61/304,319, filed Feb. 12, 2010, which is fully incorporated herein by reference.

BACKGROUND

Children and adults requiring physical and occupational rehabilitation utilize, among other equipment, rehabilitation tables. These rehabilitation tables mediate various directed manual exercises, without requiring gravity bearing by the patient's afflicted limb. Such tables have adjustments for height (to accommodate patients of different sizes) and tilt (to accommodate different tasks—such as drawing—at varying degrees of difficulty). The side facing the patient is curved inwards to facilitate reach across the table. An example of a commercially-available rehabilitation table is Convert-Able Table™ made by R.E.A.L. Design Inc. (Dolgeville, N.Y.), shown in FIG. 1.

In rehabilitation practice, the Convert-Able Table™ is not connected with any computer, such that exercise data is entered manually. Furthermore, there are no virtual reality therapeutic exercises being used or videogames played in conjunction with the Convert-Able Table.

These limitations make rehabilitation less efficient, and less motivating, thereby holding back the progress of patients. Accordingly, new and improved method and apparatus for rehabilitating patients is needed.

SUMMARY OF THE INVENTION

Various inventions relating to rehabilitation systems, structures, methods and kits are disclosed herein.

In accordance with one aspect of the present invention, apparatus for rehabilitating patients is provided. The apparatus includes a table top which, in one embodiment of the present invention, includes a table top having a low friction top, a high friction bottom, a hollow section and no legs. An electronic controller can also be attached to the table top or embedded is a hollow section of the table top. A first tilt sensor can be embedded in the hollow section of the table top so as to sense tilt on a first axis. The first tilt sensor sends a first tilt signal to the electronic controller. Also, a second tilt sensor can be embedded in the hollow section of the table top so as to sense tilt on a second axis. The second tilt sensor sends a second tilt signal to the electronic controller.

In accordance with a further aspect of the present invention, the apparatus includes a tracking circuit embedded in the hollow section of the table top that senses movement by a patient's rehabilitated arm. It can also include a power supply. It also includes a communication circuit attached to the table top and electrically connected to the first tilt sensor, to the second tilt sensor to the tracking circuit and to the electronic controller, wherein the communication circuit receives tilt signals from the first and second tilt sensor and tracking signals from the tracking circuit and wherein the communication circuit transmits the received signals.

In accordance with an aspect of the present invention, the electronic controller is embedded in the hollow section of the table top. Additionally, the communication circuit can be embedded in the hollow section of the table top.

The table top can have a layered structure that includes a plurality of modular sensing elements with a U-shaped empty section. In one embodiment of the present invention, the table top has a low friction top made of Formica. The low friction top underside can include a matrix of sensing elements. The bottom of the table top, in accordance with one aspect of the present invention is rubber. The communication circuit can be a wireless communication circuit or it can be wired.

In accordance with another aspect of the present invention, the power supply can include a charging dock connected to the power supply. The power supply can include one or more batteries.

In accordance with another aspect of the present invention, an arm support adapted to receive a forearm of the patient is provided. The arm support includes a detachable memory foam rubber attached to a base. The detachable memory foam rubber includes a Teflon cover and a bottom coded to identify the patient, such that each patient has his own rubber foam rubber pad.

In accordance with a further aspect of the present invention, the table top includes a supporting flat underside frame attached to the table top via a hinge, a handle and a manual tilt structure.

The present invention also contemplates a rehabilitation kit. The kit includes a table top having a low friction top and no legs, an electronic controller attached inside to the table top, a first tilt sensor attached to the table top so as to sense tilt on a first axis, wherein the first tilt sensor sends a first tilt signal to the electronic controller, a second tilt sensor attached to the table top so as to sense tilt on a second axis, a tracking circuit embedded in the table top that senses movement by patients and a communication circuit attached to the table top and electrically connected to the first tilt sensor, to the second tilt sensor to the tracking circuit and to the electronic controller, wherein the communication circuit receives tilt signals from the first and second tilt sensor and tracking signals from the tracking circuit and wherein the communication circuit transmits the received signals. It also includes an arm support adapted to receive the arm of the patient.

The kit, in other aspects of the present invention, also can include one or more cameras. It can also include software operable on a computer to provide instructions in using the table top and the arm support.

DESCRIPTION

U.S. patent application Ser. No. 12/192,818, filed Aug. 15, 2008 and entitled REHABILITATION SYSTEMS AND METHODS. This application describes system and methods for rehabilitation of the various parts of the body, including the shoulder, arm and hand. This patent application is hereby incorporated herein by reference. This patent application has been published as Publication Number 2009/0131225.

Figure 2:
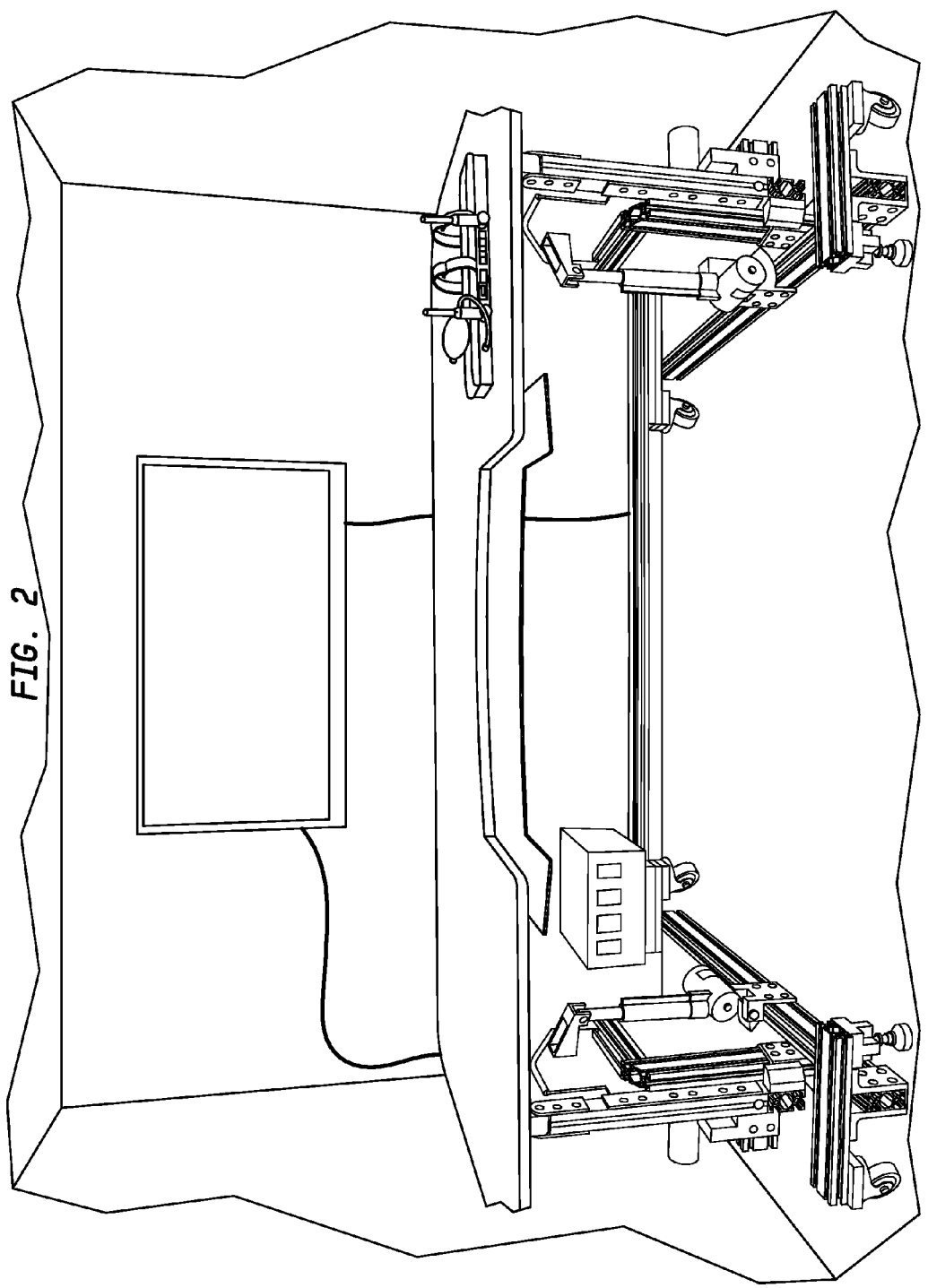
FIG. 2 illustrates another rehabilitation table.
Figure 3:
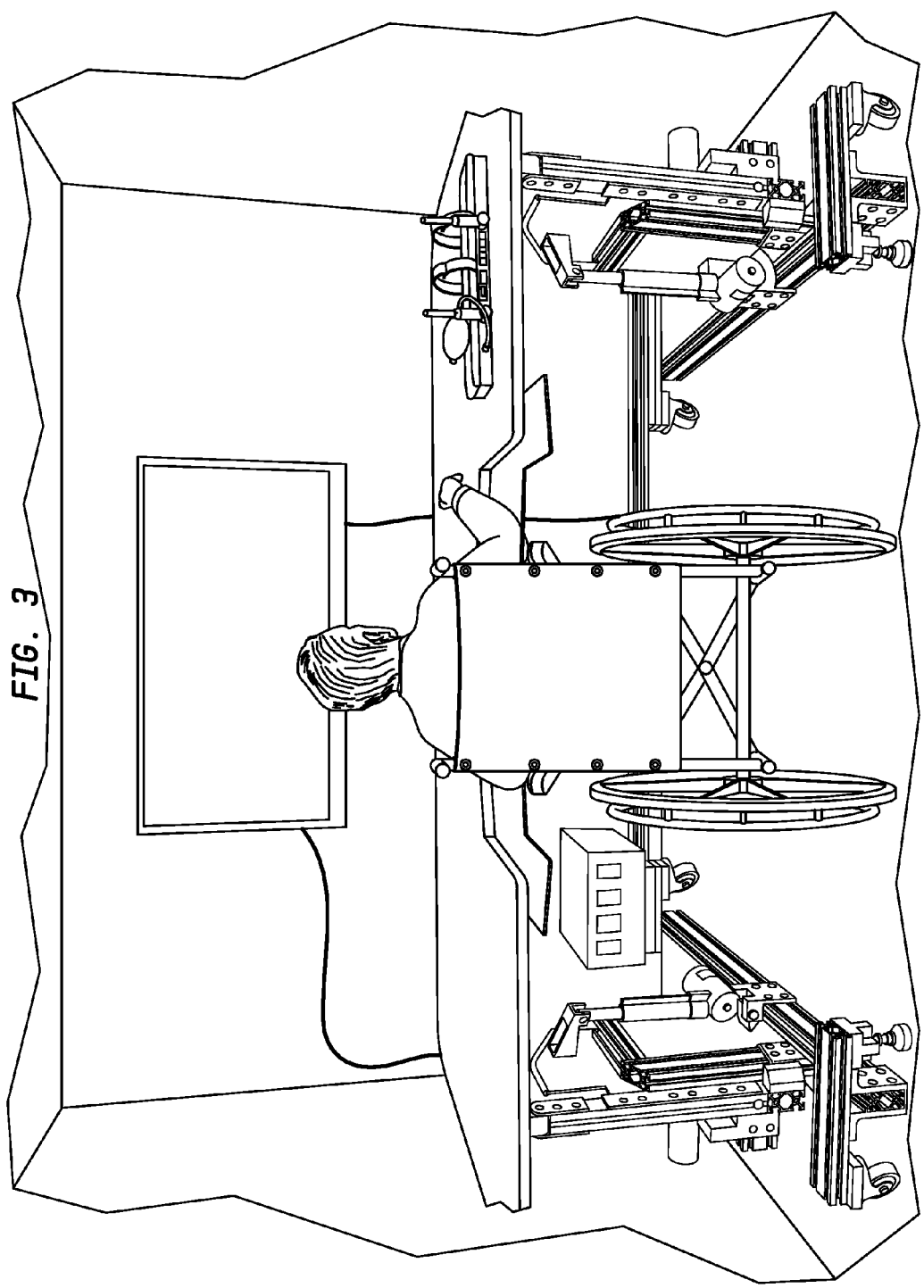
FIG. 3 illustrates the rehabilitation system in FIG. 2 being used by a patient.

FIG. 2 illustrates a prototype rehabilitation system that is more fully described in U.S. patent application Ser. No. 12/192,818. This system is referred to as the BrightArm™ system, developed by Bright Cloud International Corp (Highland Park, N.J.). It can include the following components: An arm support device is shown on the top of the rehabilitation table in FIG. 2. FIG. 3 illustrates the Bright-Arm rehabilitation table with a patient who is watching rehabilitation games on a television which is directing the rehabilitation exercises.

An instrumented rehabilitation table can provide several elements. First, a tilting low-friction table top made of any suitable material such as high-tensile plastics, carbon fiber or engineered wood, equipped with infrared LED markers at corners is provided. The table preferably has a curved edge facing the patient.

Second, a low-friction forearm support instrumented with infrared LEDs, a pressure sensor, a surface contact detection mechanism on the forearm support underside, electronics with ON/OFF switch and a wireless transmitter is provided. The top of the support preferably has memory foam for comfort, Velcro strips for attachment to the patient's forearm and a rubber pear grasped by the patient. The Velcro strips are of such dimension and placement such to allow the addition of wrist weights on the patient's arm. Such wrist weights are of the type commonly used in physical exercise or rehabilitation purposes, and are of known weight. The rubber pear is of the type commonly used in blood pressure measuring devices. The bottom of the forearm support is preferably equipped with Teflon beads (sliders) for reduced friction.

Third, a shoulder assembly worn on the opposite shoulder to the arm being rehabilitated is typically provided. The shoulder assembly comprises an infrared LED, a battery, a contact switch, and a means for attachment to the patient's shoulder closings, such as a Velcro strap or a pair of permanent magnets.

Fourth, an overhead camera provisioned with an infrared filter which is part of the vision tracking system that measures arm movement (position and orientation) on the table and shoulder leaning, is preferably provided.

Fifth, a personal computer (PC) of known art (preferably multi-core with graphics hardware acceleration and Internet connection) that runs the specialized software which synthesizes the virtualization environment and runs the rehabilitation protocol is preferably provided. The PC can be provisioned with a device that provides bi-directional wireless communication with the forearm support. The wireless link transmits real-time data to- and from the PC. With this information the PC updates the rehabilitation simulation it is running, and sends the graphics output to a large visual display facing the patient. Using this communication link the PC can also interrogate the forearm support on status, or trigger data communication packets. The display used by the system subject to aspects of present invention is any type of high-definition video terminal or TV of known art. Is preferably that such display be of sufficient dimensions (such as 55 inch diagonal or larger). Sixth, Internet communication allows game data to be uploaded on a remote clinical server to allow remote viewing by a clinician of patient exercises and progress.

In accordance with one aspect of the present invention, a system and method to transform a non-computerized mechanical therapeutic table into a virtual rehabilitation system is provided. The self-contained hollow table top with sensing elements and low-friction top work surface is in one embodiment modular and comparable in dimensions with rehabilitation table it sits of, such rehabilitation table being of known art such as Convert-a-Table. The hollow structure can be placed directly on top of existing rehabilitation tables, thereby transforming them into virtual rehabilitation systems.

In another embodiment the hollow table-top structure containing electronics and low-friction top work surface can be used at home in a tele-rehabilitation application where it is located atop a common household table.

In another aspect of this invention, the stand-alone embodiment placed on top of a common flat table can contain a tilting element and be tilted manually using a single hand, to gradate exercise difficulty, without the need of a conventional rehabilitation table. It is envisioned that the stand-alone embodiment will have manual tilting to set angles, using spacers or any other suitable mechanism of known art, and a horizontal support preferably made of light material (such as wood). The horizontal support element has high-friction rubber bottom, so to prevent movement on top of the common household table it sits on.

Figure 8:
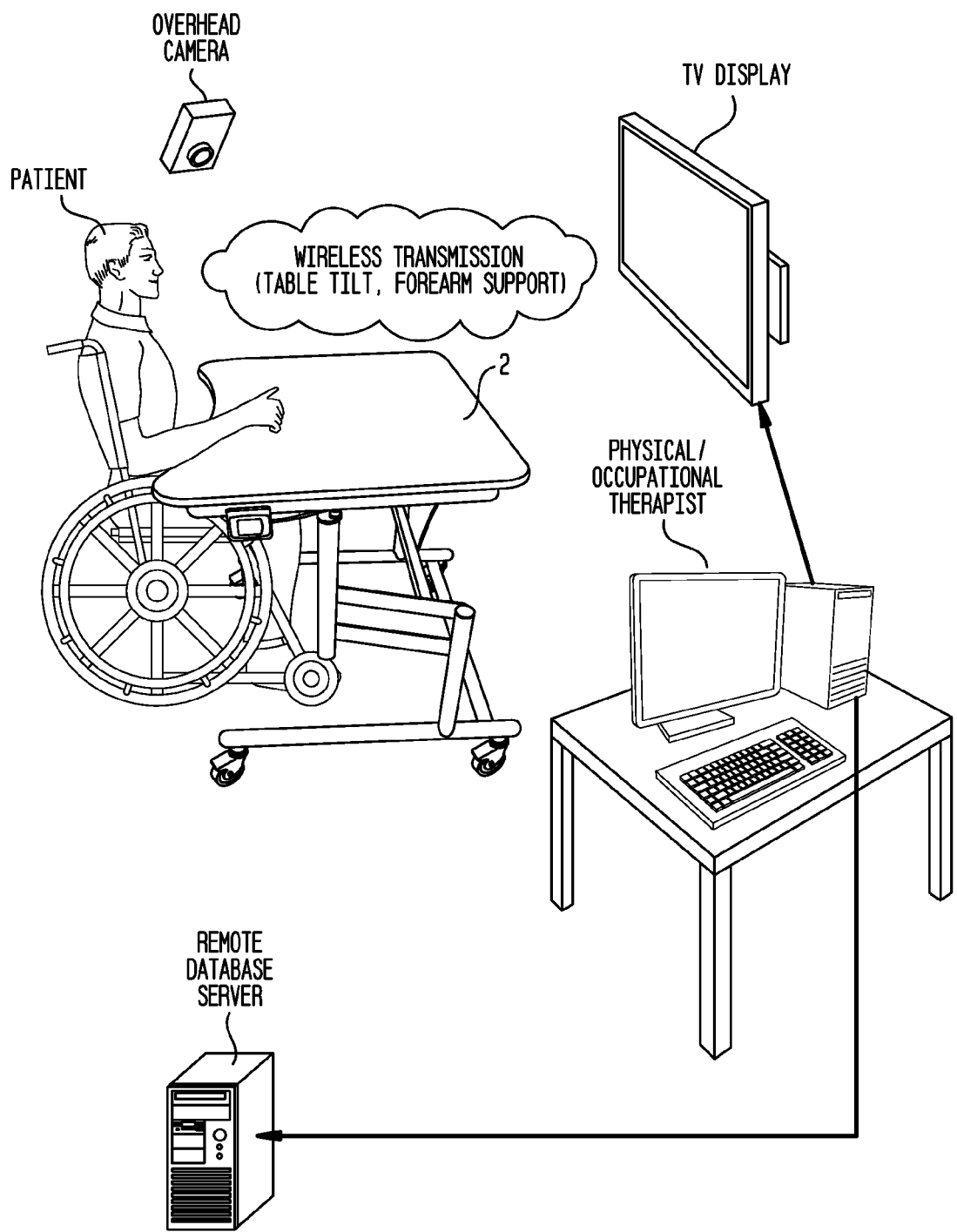
FIGS. 8 illustrates another aspect of the present invention.

The non-computerized mechanical therapeutic table can be a table that is known in the art. In accordance with one aspect of the present invention, a main component of the new system is a self-contained, instrumented work surface, that is modular and can be easily retrofitted to existing rehabilitation tables of known art. This component is illustrated in FIGS. 4 and 8.

Figure 4:
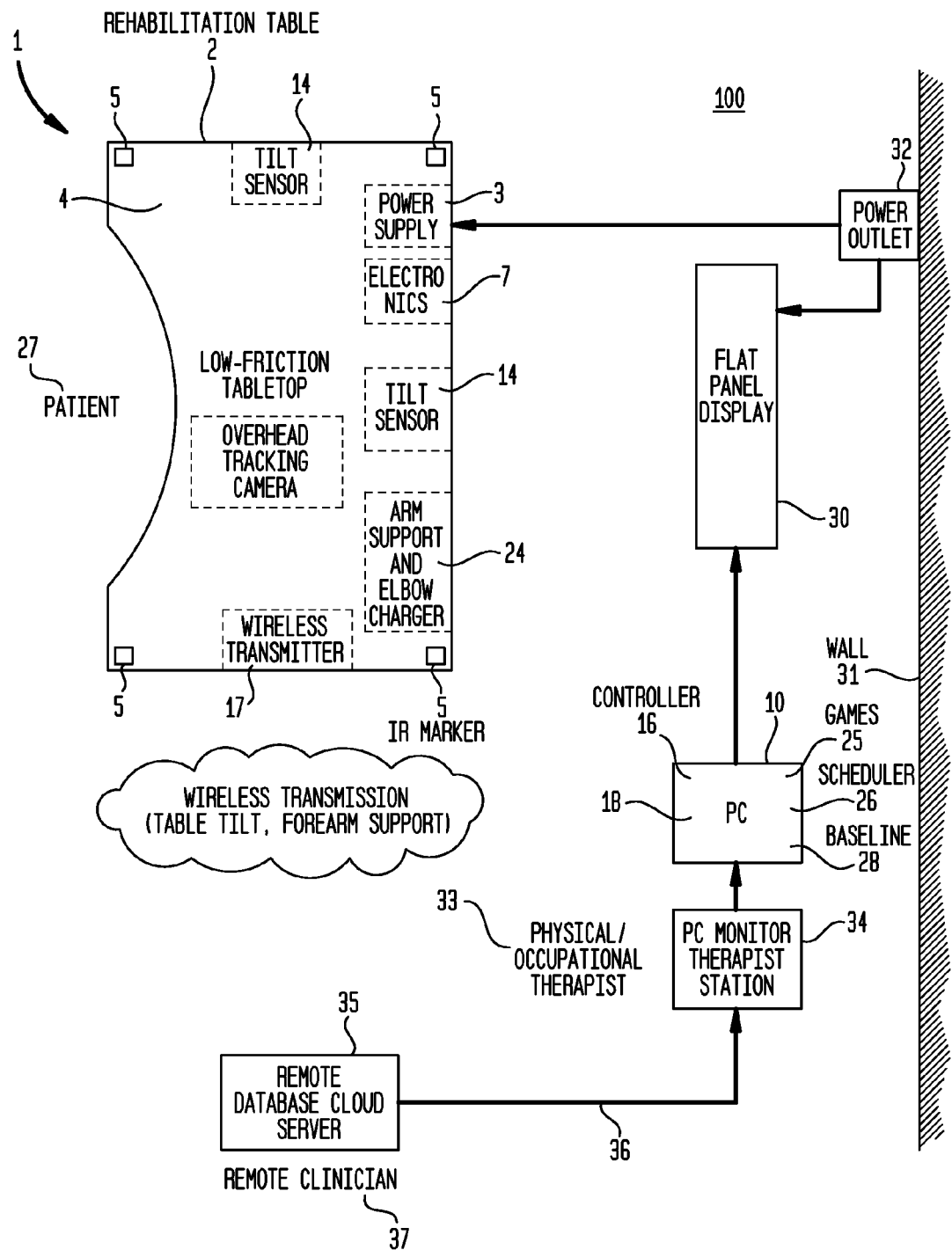
FIG. 4 illustrates a rehabilitation system and device in accordance with further aspects of the present invention.

In FIG. 4, the modular work surface is provisioned with electronics embedded in a lightweight, low-friction structure built with suitable materials of known art such as low-friction, ultra high molecular weight polyethylene (UH-MWP).

In accordance with one embodiment of this invention, the work surface may contain movement detection sensors which may be capacitive, resistive or any other known art to detect the motion of the instrumented arm support located on the instrumented table top work surface. The direction and rate of motion are calculated by a specialized electronic controller embedded in the work surface from signals or data it receives from the motion sensors and reported via a wireless data link to the PC which runs the virtualization environment. The controller is implemented with hardware elements of known art which may include: a single or a plurality of microprocessors, a means to interface with the other components of the work surface, a power supply and power management circuitry and a means of communication to the PC which runs the virtualization environment. In another embodiment of this invention, the motion of the arm support is detected by means of non-contacting optical proximity sensors of known art embedded either in the work surface or the arm support. An associated controller translates the received optical signals into positional data which it reports to the PC that runs the virtualization environment.

In yet another embodiment of this invention the motion tracking is performed by a vision system as further described below. The work surface has embedded infrared (IR) LED markers which are part of the vision tracking component of the system (previously described in 818). The LEDs are powered by a low-voltage power supply also embedded in the low-friction hollow work surface. A plurality of IR cameras of sufficient resolution that is part of the same vision tracking system is mounted overhead (i.e.: on the ceiling or false ceiling) by any suitable means of known art. Data from the camera is transmitted to the PC running the visualization environment and the rehabilitation exercises, to determine the real-time arm position and any trunk leaning.

In accordance with one aspect of the present invention, the instrumented work surface is positioned atop the mechanical structure of a conventional therapy table of known art which allows it to be adjusted in height to accommodate a wide range of patients and tilted to gradate the amount of weight bearing on the arm/shoulder being trained. The height and tilt angle of the instrumented work surface are sensed by a plurality of suitable electronic sensors of known art placed at suitable locations in the work surface. Tilting can be either manual or electrical, in which case electrical actuators need to be retrofitted to the rehabilitation table as well.

The work surface instrumentation is controlled by a specialized electronic controller also embedded in the table top. The specialized controller is built using hardware elements of known art and includes a power supply. The work surface sensor output signals are processed by the specialized electronic controller and sent to the PC which runs the virtualization environment and rehabilitation exercises by means of a wireless communication link of known art.

In another aspect of this invention, the work surface is provisioned with suitable proximity detectors of known art to detect an accidental contact with the patient's legs while the work surface and the table mechanism supporting it are in motion being adjusted for height and/or tilt. Should a patient contact occur the electrical actuators are immediately cut-off from their power source and an alarm is sounded.

The same wireless communication link is used to send data on grasp pressure measured by the forearm support sensor, as well as data from the non-contacting proximity detector of known art that detects loss of contact between the forearm support and the table surface, to the PC. This is described, for example, in U.S. patent application Ser. No. 12/192,818, filed Aug. 15, 2008 and entitled REHABILITATION SYSTEMS AND METHODS.

The data transmission should be done frequently, such that updated information is instantaneously received by the PC. Transmission frequency is at industry-standard rates which should be adjustable to allow the PC to receive, process and respond to the data inputs in a suitable time interval.

In accordance with another aspect of the present invention, the work surface can also incorporate means of non-contact charging the forearm support battery as well as that in the shoulder assembly. It is envisioned that charging can be done by untethered (wireless) means (such as used in Duracell's MyGrid charging pad). The pad is preferably placed at the extremity of the work surface furthest from the patient, such that it does not interfere with any of the arm reaching exercises. The forearm support and the shoulder assembly is preferably placed on top of the embedded charging pad overnight or at any other time when the rehabilitation system is not in use.

Figure 1:
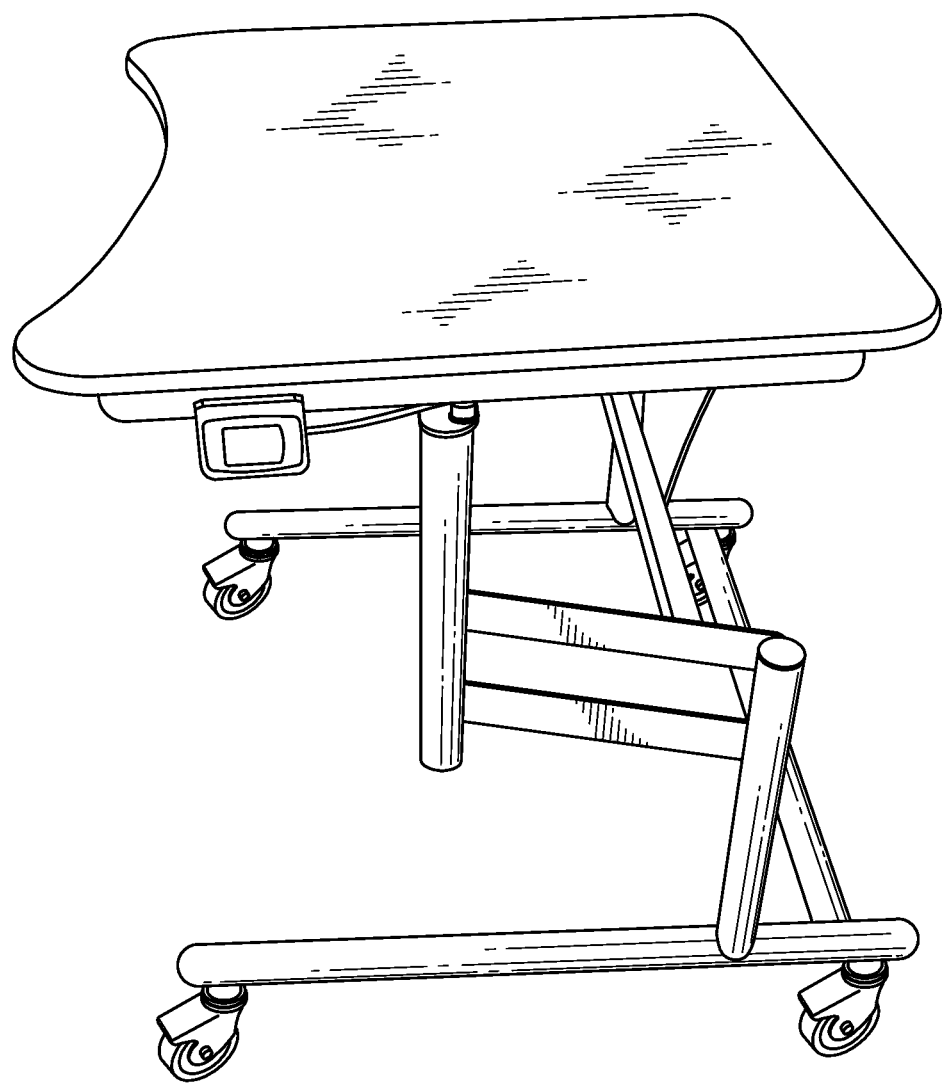
FIG. 1 illustrates a prior art rehabilitation table.

The modular, instrumented table top that can be retrofitted onto existing mechanical tables is illustrated in greater detail in FIGS. 4 to 8. In FIG. 8, a modular table top 1, in accordance with an aspect of the present invention is illustrated. The modular table top 1 sits on top of a rehabilitation table 2 such as the table shown in FIG. 1. The table of FIG. 1 is not shown in FIG. 4.

The table top 1, in accordance with an aspect of the present invention as shown in FIG. 4, includes a power supply 3, a top surface 4, infrared markers 5, electronics 7, a first tilt sensor 14, a second tilt sensor 14, a wireless communication circuit 17 and an arm support structure 24. A patient 27 sits at the table 2 resting the affected arm 11 on instrumented forearm support 21. Also provided as part of the arm support 21 structure is a pressure sensor 22, a proximity sensor 20, a battery 22. The arm support structure 24 is shown in more detail in later drawings. The patient 27 typically wears a shoulder assembly 23.

The table top 1 is connected to a power outlet 32. An overhead camera can be positioned over the table top 1. The overhead camera allows a patient's movements, particularly the movements of the arm, to be tracked. The overhead camera can also allow a rehabilitation session to be monitored and/or recorded.

The table top 1, in accordance with an aspect of the present invention, includes no legs. Instead the high friction bottom surface, such as rubber, is provided. This allows the structure to be placed atop other tables, and prevents slipping. It is envisioned that additional fastening means, such as clamps 1000 can be used at the corners of table 2 to prevent movement of the instrumented table top once attached to the conventional rehabilitation table.

A display 30 can be mounted on a wall 31 in accordance with an aspect of the present invention. A PC 10 drives the display 30. The PC 10 includes games 25, a scheduler program 26, a baseline program 28 and controllers 16. A therapist 33 observes a monitor 34 connected to the PC 10 so as to be able to monitor the rehabilitation session. In accordance with an aspect of the present invention, the PC 10 with monitor 34 is connected to a cloud server 35. A remote clinician 37 can monitor the session through the cloud.

Figure 5:
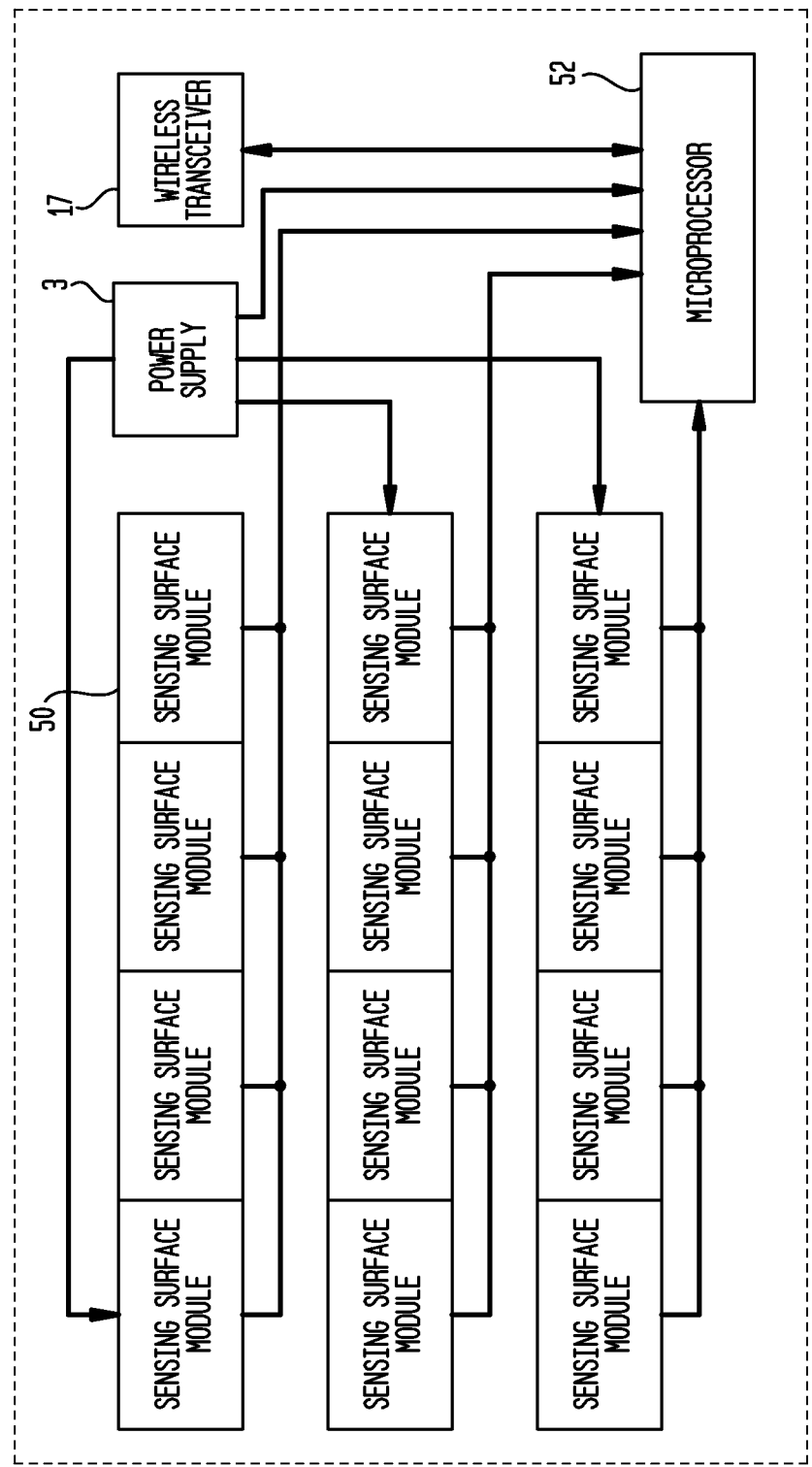
FIG. 5 illustrates a block diagram of the sensor matrix elements in a table top of the present invention that form a tracking circuit.

The instrumented table top 1 in one embodiment of the present invention, includes a tracking circuit. The tracking circuit is shown in FIG. 5. It includes a plurality of sensing surface modules 50. These are driven by the power supply 3. Each of the sensing surface modules 50 are connected to a microprocessor 52 which acts as an electronic controller to collect electronic signals generated by various electronics associated with the table 2. The microprocessor 52 collects these signals, transforms the signals into a preferred form for transmission, and then sends the signals to a wireless communications circuit 17. The wireless communications circuit 17 then transmits the signals. By way of example, the signals can be transmitted to the PC 10.

Figure 7:
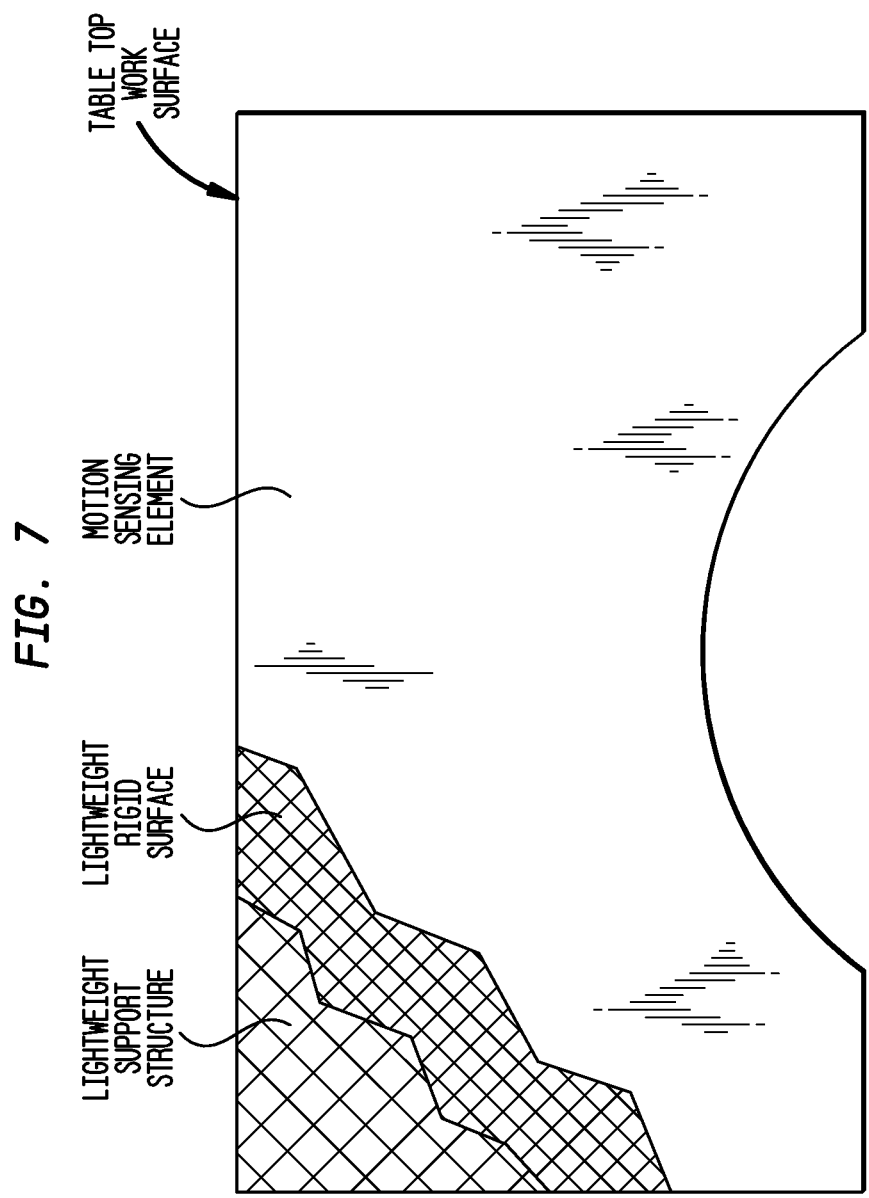
FIG. 7 illustrates the layered structure of the instrumented table top surface in accordance with a further aspect of the present invention and a method of using the invention in accordance with another aspect of the present invention.

The motion sensing modules may be implemented with any known art such as: capacitive, optical transmissive, optical reflective, optical interruptive or any other suitable technology of know art. The specific module technology is dependant on the particular requirements of each of the described embodiments of the present invention. The modules are affixed to the table top surface facing the patient and may be either one continuous unit or a plurality of individual modules arranged in a tile pattern as depicted in FIG. 7. The sensor modules detect the presence and motion of the forearm support across the table top and provide data inputs to the microprocessor 52. The microprocessor calculates the position of the forearm support and reports it to the PC 10 by means of a wireless transceiver 17 of any suitable known art as described above.

The outputs of the tilt sensors 14A and 14B are sent to the microprocessor 52. Outputs of the arm support 24 can also be sent to the microprocessor 52. The status of the power supply 3 can also be monitored by the microprocessor 52. The microprocessor 52 assembles all of the signals it receives and transforms it into a transmission signal. The microprocessor 52 sends the transmission signal to the communication circuit 17, which transmits the transmission signal wirelessly or via a wired circuit. The PC 10, for example, can receive the transmitted signal and can transmit signals to the instrumented table top.

Figure 6:
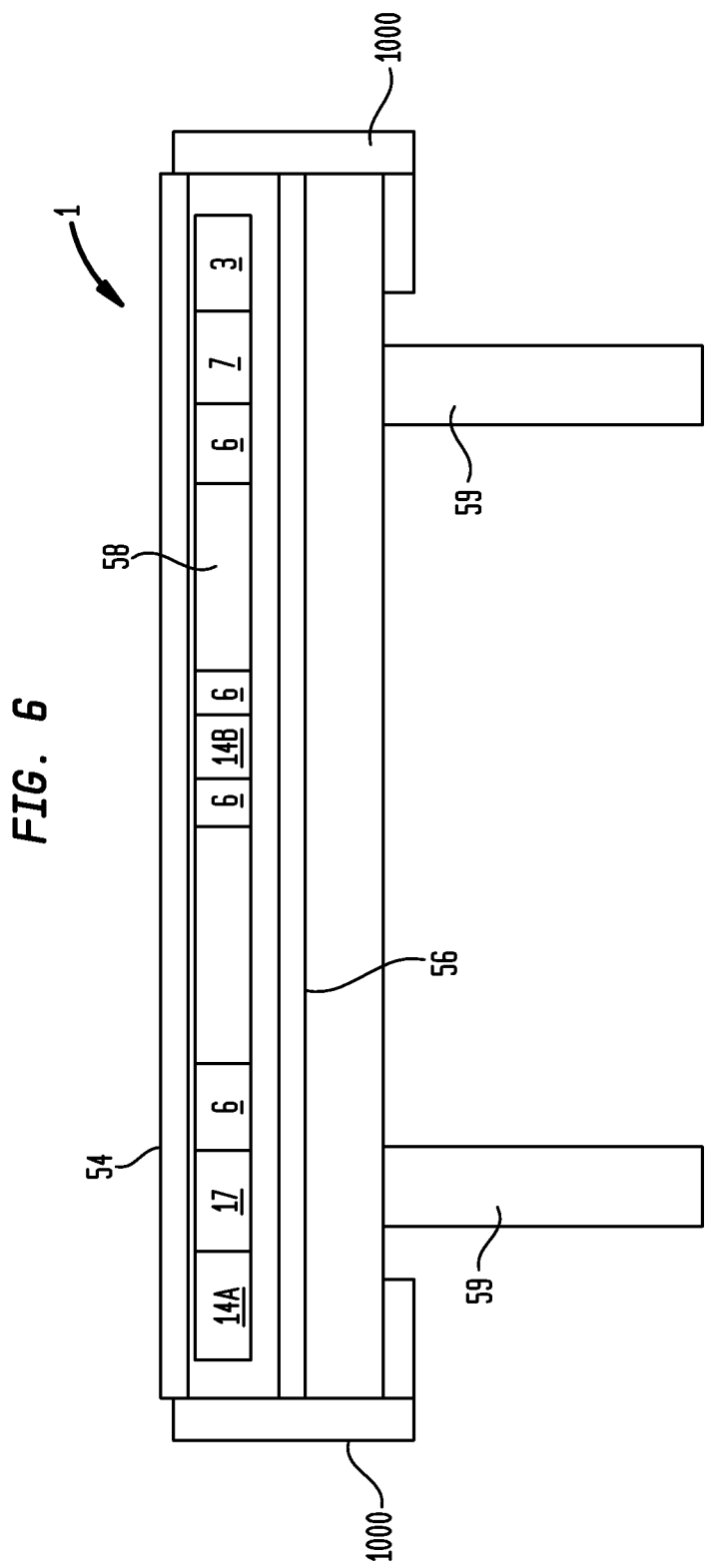
FIG. 6 illustrates a lateral view of the instrumented rehabilitation table top placed on top of the conventional rehabilitation table, in accordance with a further aspect of the present invention.

In accordance with one aspect of the present invention, the table top 1 is constructed with a hollow section in which the electronics are fit. This is illustrated in FIG. 6. The table top 1 has a top surface 54. The top surface 54 can be laminated onto the base 55. The top surface 54, in one embodiment, is Formica. The surface 54, however, can be any type of low friction surface such that a patient's arm support structure can slide easily on the top surface 54. Irrespective of the specific embodiment of this invention, it is preferred that the coefficient of static friction between the work surface and the patient arm support not exceed a value of 0.2. Furthermore, it is preferred that no liquid or dry lubricants are used to achieve this value. It is also preferred that the corresponding coefficient of kinetic friction between the surface and the patient arm support be equal or less than the coefficient of static friction referred to above.

The table top 1 also has a bottom surface 56 that, when in use, rests on the mechanical table structure 59. The structure 59 can be, for example, a table such as shown in FIG. 1. However, the structure 59 can be any other available table as well. The bottom surface 56 can be laminated onto the base 55. The bottom surface 56 preferably has a higher coefficient of friction than the top surface 54. The bottom surface 56 is preferably constructed of rubber. The higher coefficient of friction associated with bottom surface 56 the instrumented table top 1 allows it to be placed on the structure 59 and used by a patient without the table top 1 slipping on the structure 59. Further, clamps 1000 can be attached at ends of surface 56 connecting it with structure 59 to further prevent sliding.

The table top 1 preferably has a hollow section 58. The hollow section 58 can simply be a cut out of the bottom of the instrumented table top 1 so that it is not surrounded by the top and bottom surfaces of the table top. The electronics associated with the instrumented table top 1 in accordance with the various aspects of the present invention are preferably housed within the hollow section 58 of the table top 1. Thus, the tilt sensors 14A and 14B are housed in the hollow section 58. The sensing surface modules 6 are also preferably mounted in the hollow section 58. The communications circuit 17 is also preferably mounted in the hollow section 58. The various other associated electronics 7 are also preferably mounted in the hollow section 58. The power supply 3 is also preferably mounted in the hollow section 58.

The power supply 3 comprises batteries in accordance with an aspect of the present invention. The power supply 3 can include a docking station to allow the batteries of the forearm support to be charged.

The communications circuit 17 can be a wireless communication circuit of known design. The communications circuit 17 can also be a circuit that provides communications over a wired transmission line, as is well known in the art.

While all of the electronics and sensors can be located in the hollow section of the table 1, they can also be attached to the table in a number of different ways. For example, they could be attached to one of the surfaces of the table top 1.

The table top 1 can also be made with a layered construction as shown in FIG. 7. Layered construction has a top low-friction surface (work surface) comprised of an array of motion sensing elements. Such elements are arranges in a matrix of sufficient size to accommodate patient's arm reach movement and are cut in the area where the patient sits. In the illustration a lightweight support structure such as carbon fiber honeycomb is contained between two lightweight rigid surfaces made of carbon fiber or similar composite materials of known art. The surface of the table to facing the patient constitutes the work surface referred to in this invention. The work surface may be used as is in the non-instrumented embodiment referred to in this invention or provisioned with motion sensors as described in 0045 and elsewhere in this invention. The motion sensors may be a single, continuous element or a plurality of elements arranged in a tile pattern as described in paragraph 0050.

FIG. 8 illustrates the use of the table top 1 in accordance with an aspect of the present invention. The table top 1 is placed on top of rehabilitation table 2. The PC runs a program that displays in instructions via a display to a patient who performs rehabilitation acts in accordance with the instructions. The tilt position of the table top 2 is sensed by the tilt sensors 14A and 14B embedded on the instrumented tabletop 1. The position of a patient's arm is sensed either by an overhead camera or via the sensing surface modules 50. These sensors generate signals which are sent to the microprocessor circuit 52. As described before, the microprocessor circuit 52 transforms the signals from the sensors into a transmission signal which is sent to the communication circuit 17. The communication circuit 17 then transmits the transmission signal.

Figure 9:
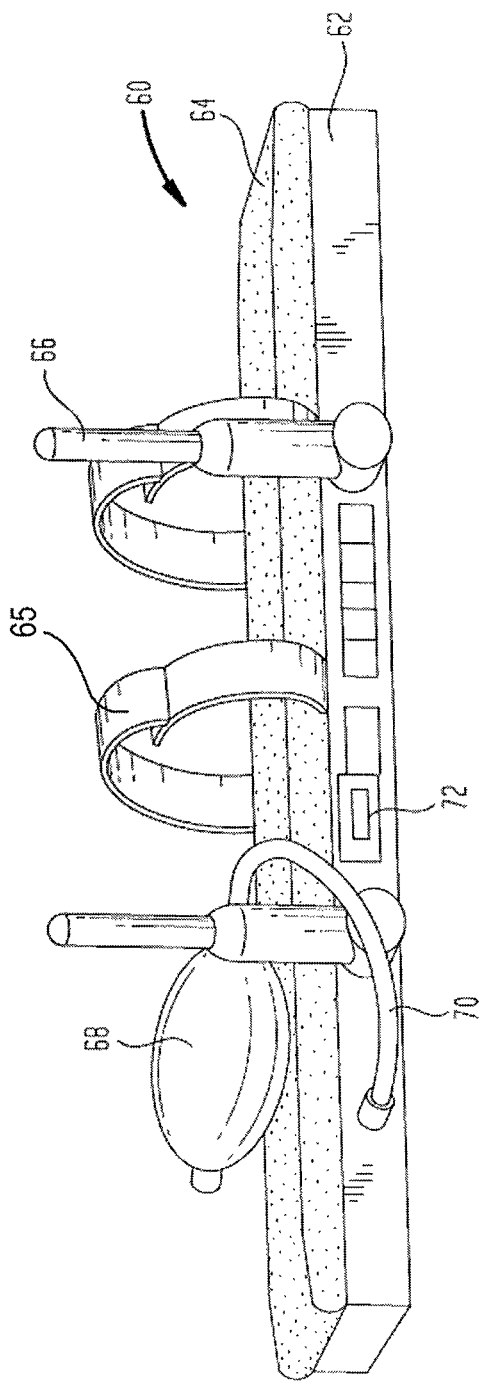
FIGS. 9 to 14 illustrate an arm support in accordance with further aspects of the present invention.

In accordance with another aspect of the present invention, an arm support structure is provided. FIG. 9 illustrates the arm support structure 60 in accordance with an aspect of the present invention. The arm support structure 60 includes a base 62. It also includes a top structure 64. It further includes arm straps 65, infrared LED locating posts 66, a rubber pear 68 meant to be squeezed by a patient, a tube 70 and electronics 72. In operation, a patient's arm rests on the top structure 64 and is held in place by the straps 65 (preferably made of Velcro). The patient moves the arm support structure 60, for example, on top of the table top 1, and squeezes the bulb 68 in accordance with rehabilitation instructions provided by the rehabilitation system, in accordance with an aspect of the present invention.

Figure 10:
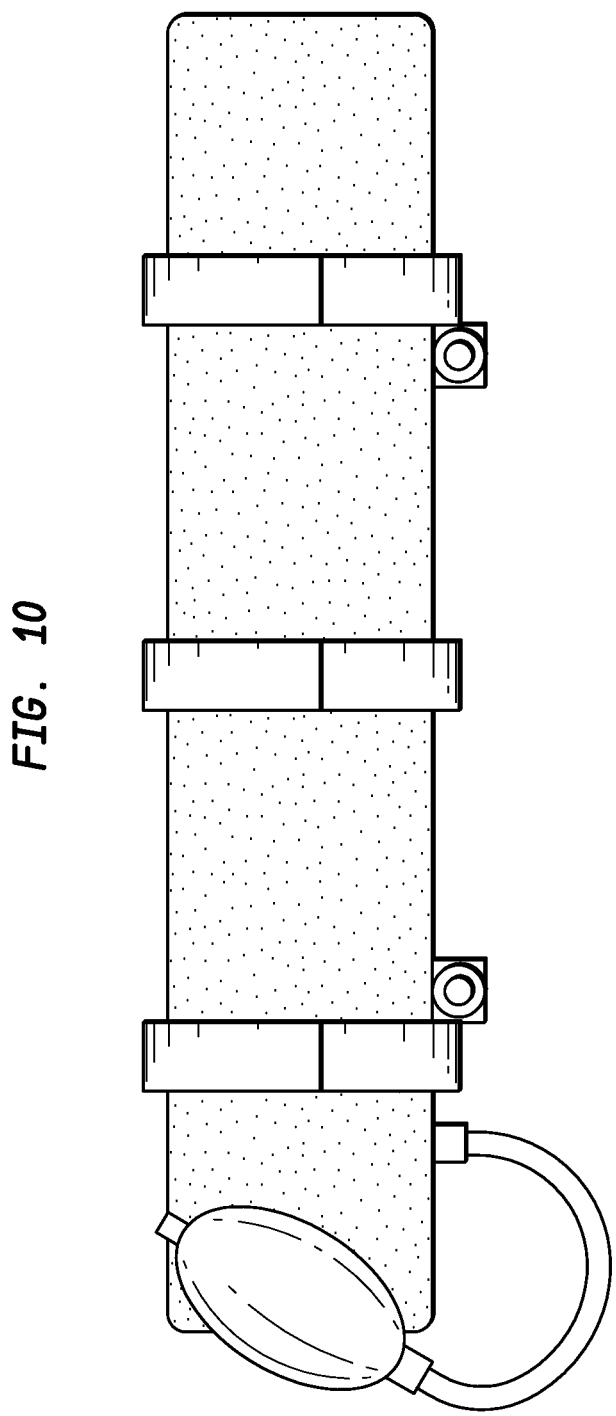
Figure 11:
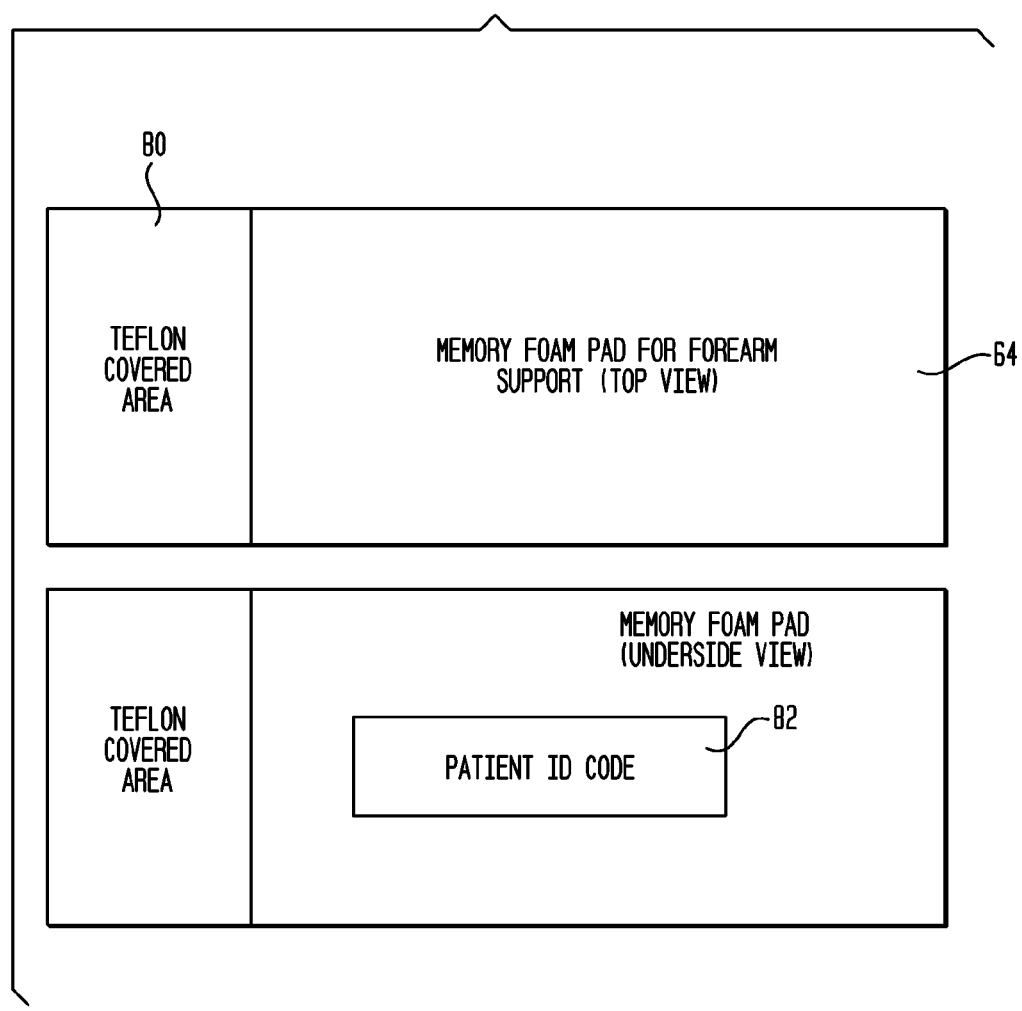

FIG. 10 illustrates the arm support structure 60 from a top view. FIG. 11 illustrates the top structure 64. A top view of the structure is shown first and a bottom view is shown second. The top structure 64 is preferably a memory foam pad. This increases the comfort. It has an area 80 covered by Teflon, or a Teflon like material. A patient identification code 82 is provided on the bottom surface of the top structure 64. The code 82 can be a UPC code or the patient's numerical code, or the patient's name. Thus, each patient has their own top pad.

Figure 12:
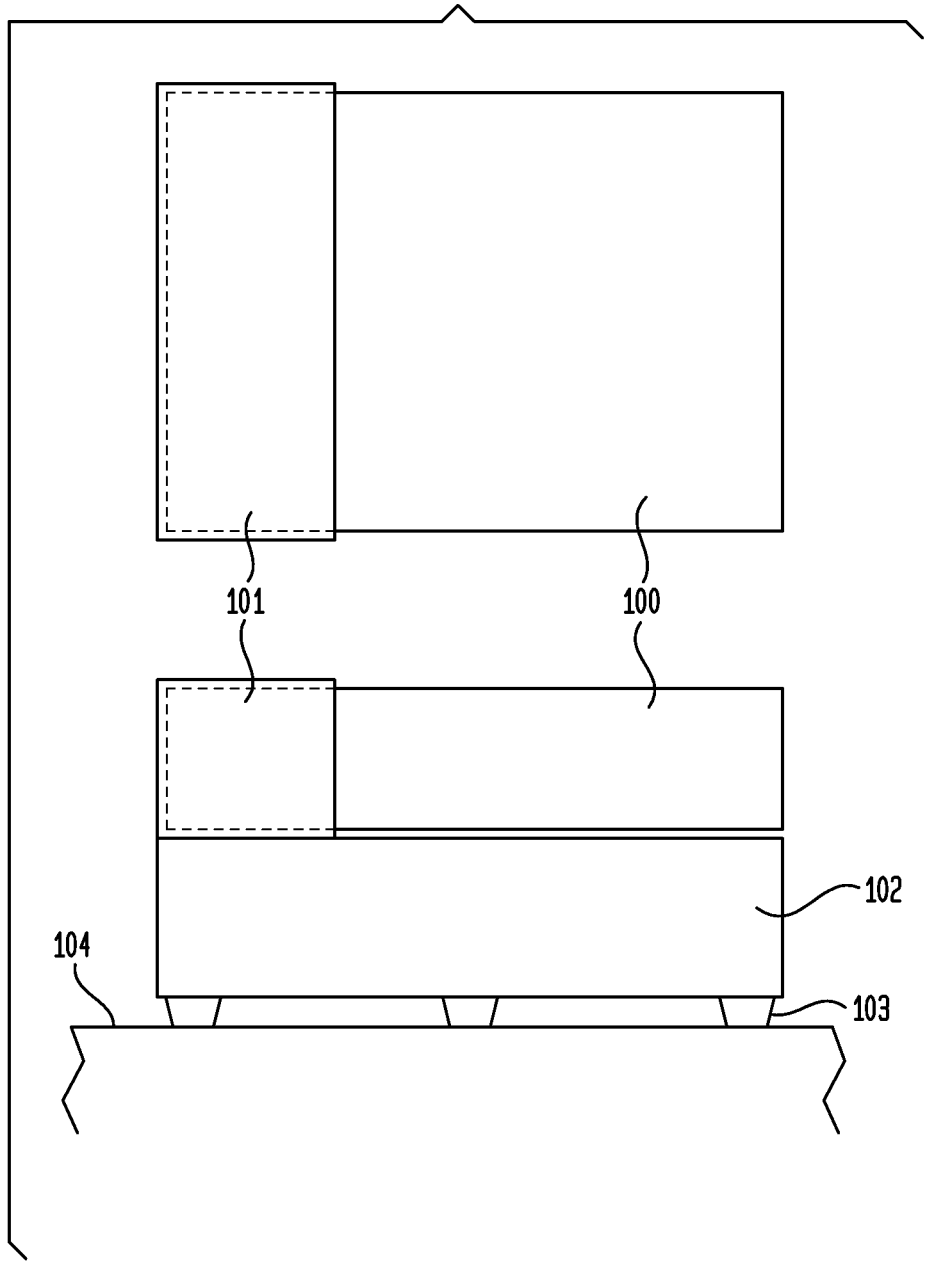
Figure 13:
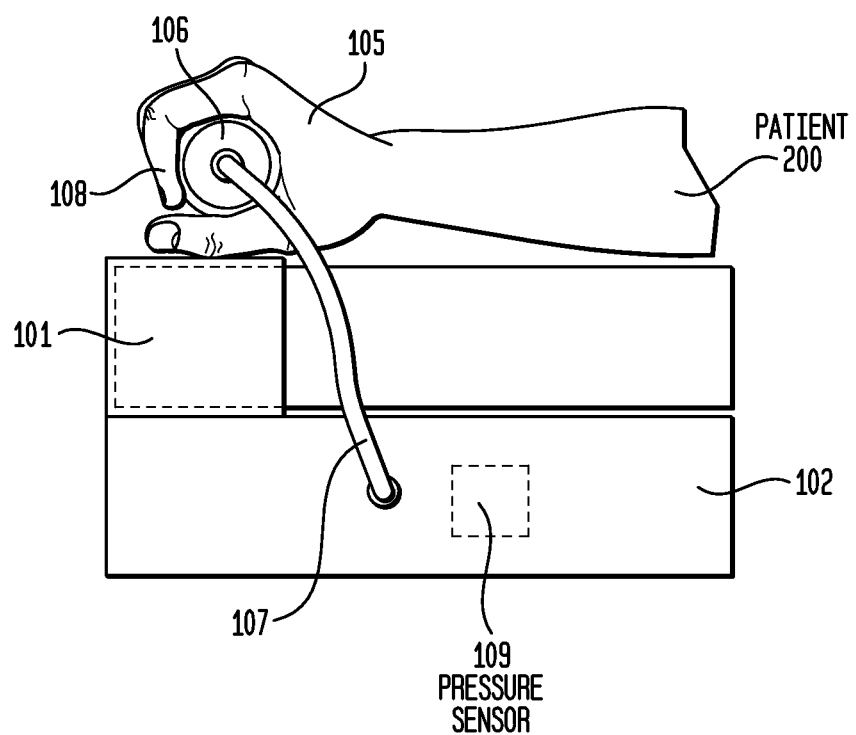

FIG. 12 illustrates top and side views of the arm support structure 60. In this figure, the arm support structure 60 is shown to include the memory foam pad 100, the Teflon wrap 101, a base section 102, low-friction spacers 103. The device rests on the table top 104 which has a low friction surface to allow the arm support structure to be moved easily by a patient. The memory foam pad 100 covers the top of the forearm support base 102. The low-friction spacers 103 are affixed to the bottom of the base 102. The Teflon wrap covers a section 101 of the memory foam pad 100. Thus, referring to FIG. 13, when a patient's hand 105 grasps the rubber pear-like deformable element 106 connected by tube 107 to forearm support base 102, the patient's fingernails 108 are prevented from digging into foam pad 100, allowing the patient 200 to better grasp rubber pair 106, thus improving the accuracy of grasp strength measurement by pressure sensor 109 located inside the forearm support 102.

Figure 14:
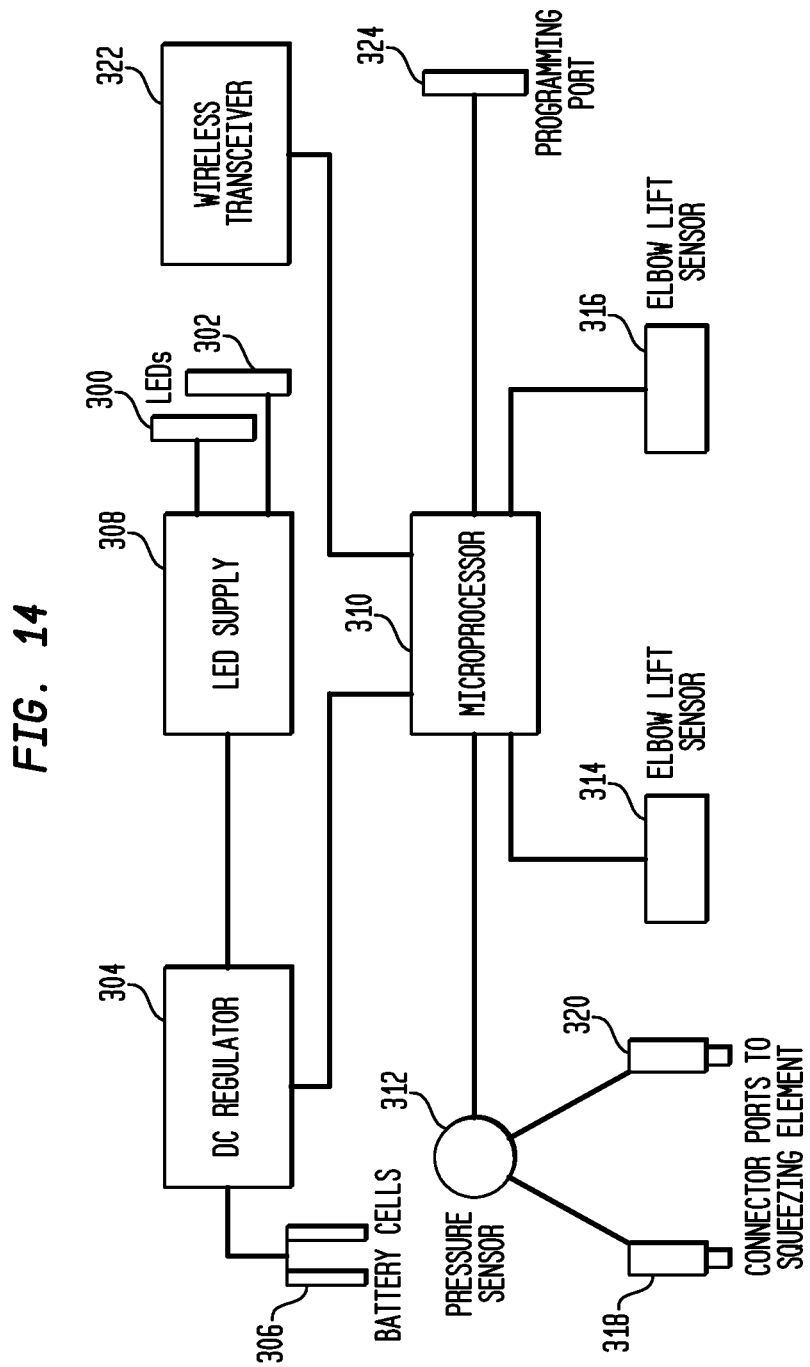

FIG. 14 illustrates the electronics provided in the arm support structure in accordance with one aspect of the present invention. Forearm support electronics comprise a pair of LEDs 300 and 302 (preferably infrared) powered by a DC regulator 304 which receives current from an array of rechargeable DC batteries 306. Driver circuitry 308 is provided. LEDs 300 and 302 are viewed by overhead digital cameras to determine position and orientation of the arm support on the instrumented therapeutic table top, in accordance with one aspect of the present invention. The DC regulator 304 also powers a microprocessor 310 which also received data from a pressure sensor 312 and from two contact lift sensors 314 and 316. The contact lift sensors 314 and 316 are on the underside of the forearm support structure and detect when patient lifts an arm off table low-friction surface. The pressure sensor 312 has two input ports 318 and 320, where the tube from the rubber pear grasped by the patient is connected. Depending whether the left or right arm needs therapy, the rubber pear tube is mated with one or the other of the two connectors. A wireless transceiver 322 transmits grasp strength data to the PC, to be used in therapeutic games in connection with vision tracking data. In accordance with one aspect of the present invention, at least 100 grasp strength measurements are transmitted every second. Nothing in the embodiment of FIG. 14 is intended to limit the types of hardware elements which can be used to realize to any specific type or manufacturer. The electronic controller 310 is also provisioned with a data interface port 324 of known art such as: RS-232, USB, SPI, IIC, J-TAG or any other known art for the purpose of programming, verification or testing the electronic controller 310.

In accordance with another aspect of the present invention, the PC runs the specialized virtualization environment and the rehabilitation exercises which are in the form of interactive games specifically developed for rehabilitation. The PC can also house the specialized session scheduler software that sequences the exercises depending on the patient specific protocol. Additional software on the PC performs the baseline for arm reach and grasp strength, such that each exercise automatically adapts to each patient at every session.

Such PC rehabilitation software is described in co-pending U.S. patent application Ser. No. 12/942,668, filed Nov. 9, 2010, which is fully incorporated herein by reference.

In accordance with a further aspect of the present invention, graphical output data is sent to a suitable video display of known art, such as an HDTV mounted on the wall opposite the patient. The positioning of the TV is preferably such that it allows for comfortable viewing without being obstructed by the table tilt.

A remote clinical server is preferably also part of the system receives the exercise and patient data and allows clinicians located remotely to supervise the patient and review the progress of the treatment either in real-time or at a later time.

The system of the present invention can function with or without a therapist present on-site. It also enables home-based therapy in tele-rehabilitation embodiments.

Figure 15:
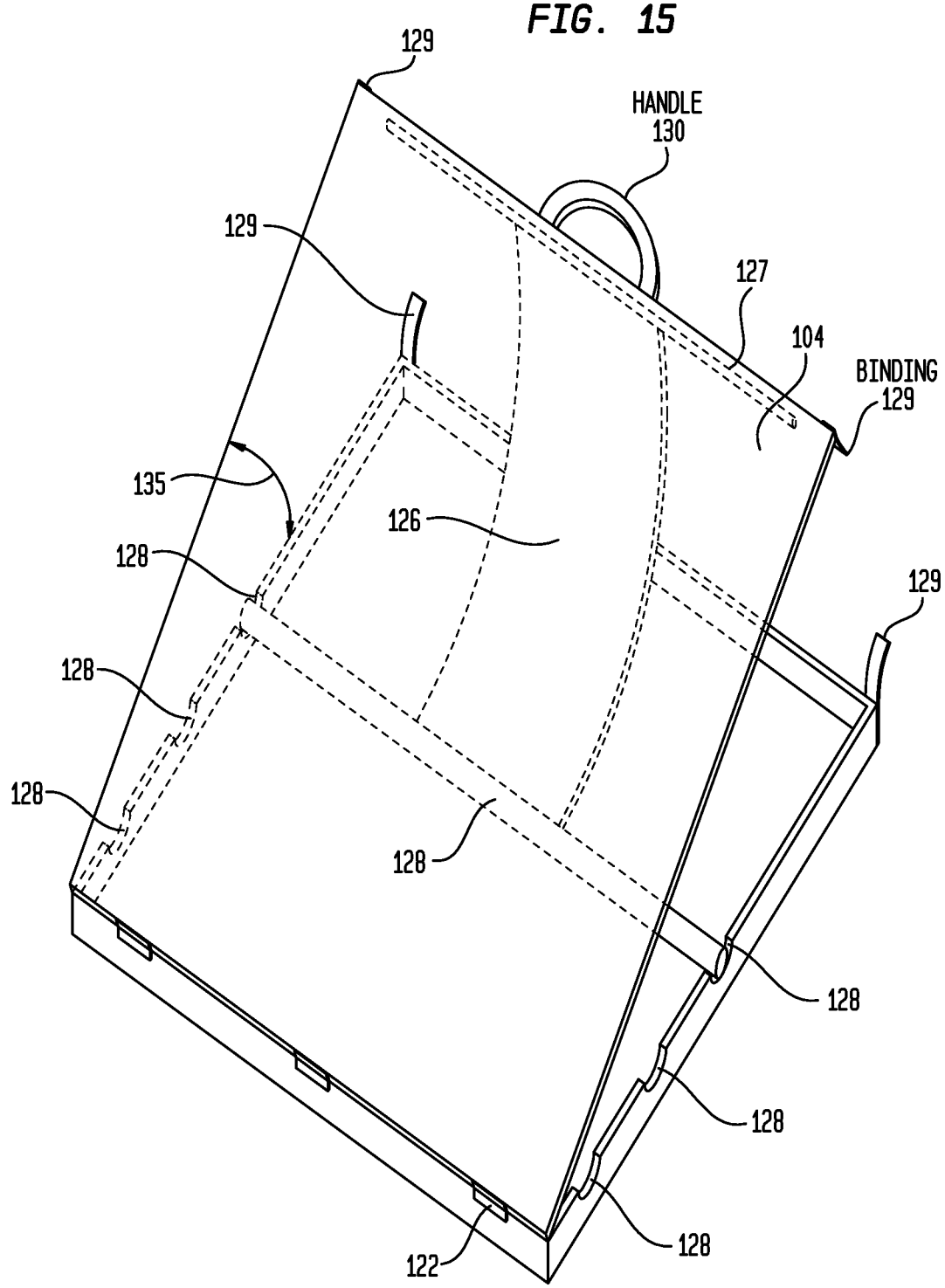
FIG. 15 illustrates a table top tilting mechanism in accordance with a further aspect of the present invention.

FIG. 15 illustrates another embodiment of the invention. This embodiment is particularly useful in arm therapy taking place in a patient's home. It is essentially a modular electronic rehabilitation table in a suitcase shape. The suitcase structure includes an upper surface 104 and a lower frame 121. The electronics and the instrumented table top 1 described earlier can be located in the upper surface 104 or within the lower frame.

The tilting mechanism of work surface 104 is comprised of an assembly of T bars 126 127 to be operated by a single arm of the patient. Tilting angle 135 of work surface 104 vs. support frame 121 is adjusted by moving T bar 135 in one of multiple grooves 128. Patient pushes on element 126 to lower the work surface 104, or pulls up on element 127 to increase the tilt. To accommodate this motion element 127 rotates about its attachment to surface 104 underside. When the work surface 104 is made horizontal, it can mate with support frame 121 using bindings 129. In that case patient 200 can transport the tabletop assembly by holding on to handle 130.

Figure 16:
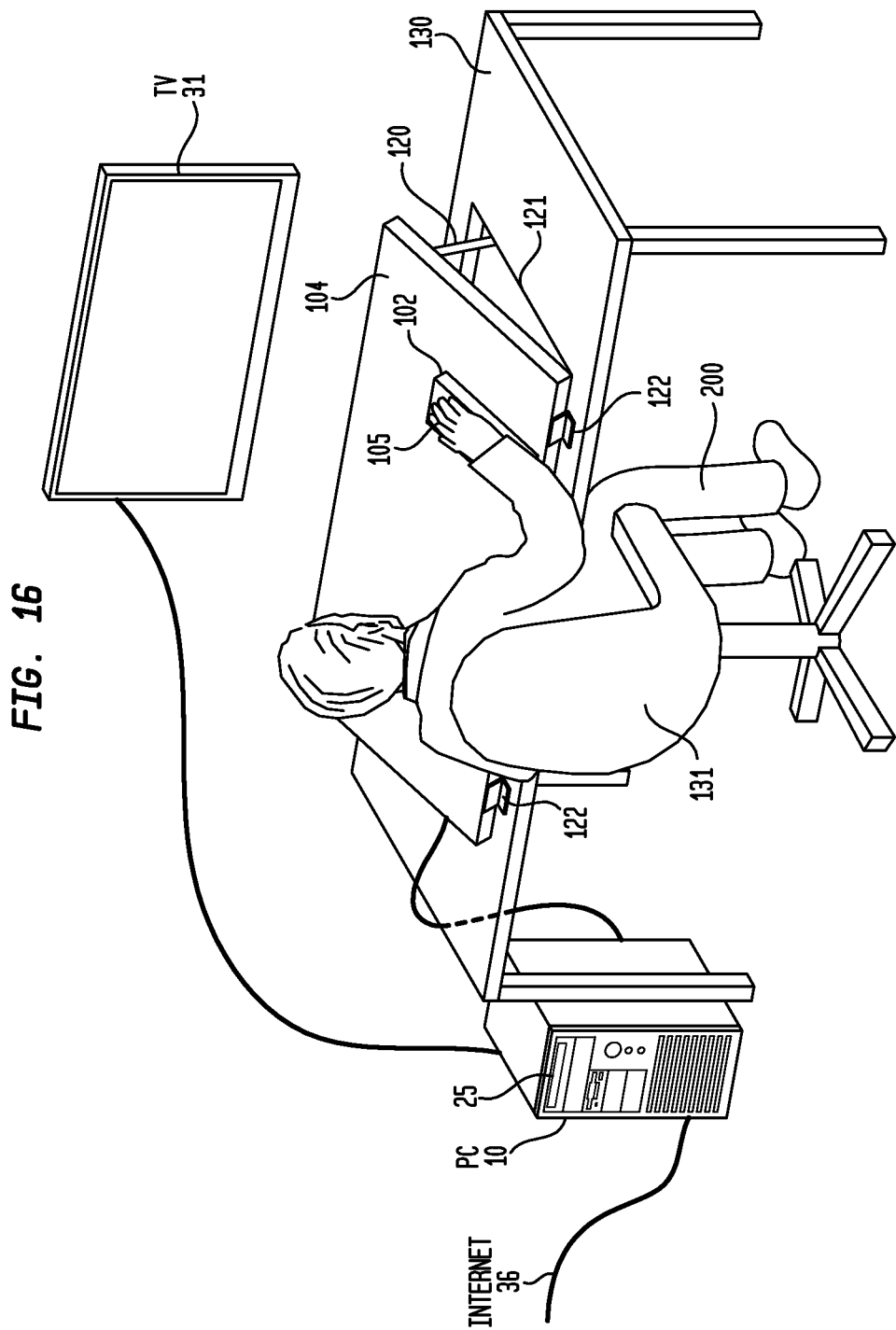
FIG. 16 illustrates the preferred use of the present invention in a patient's home.

According to FIG. 16, the patient 200 sits in chair 131 at a regular table 130 facing a TV 31. In this embodiment of the present invention, hollow work surface 104 is placed on top of table 130 and tilted using spacers 120. It is envisioned that two spacers will suffice, to the left and right of the patient. Alternately the tilting element described in FIG. 15 can be used. Spacers 120 tilt work surface 104 versus supporting frame 121 and attach to same. It is envisioned that supporting frame 121 is modular with work surface 104, such that they form one hinged assembly using hinges 122. For patients 200 who are weak, spacers 120 are retracted, such that the work surface 104 becomes flat. Patient 200 puts his arm 105 to be rehabilitated on top of forearm support 102 previously described, such that patient's hand grasps rubber element 106. When grasping rubber pear 106 the arm is positioned such that fingernails 108 are located on top of Teflon surface 101 of the rubber pad 100.

It is further envisioned that in a home tele-rehabilitation application the invention can use a regular (digital) TV as display, and the patient will be sited at the regular household table where the invention is placed and facing the TV.

In one aspect of this invention the sensors built in the work surface 104 are sufficient to track the movement of the forearm support and no overhead camera is needed.

In accordance with one aspect of the present invention, a method of rehabilitation a patient is provided by using an existing mechanical table top. In accordance with the method, a instrumented table top having a low friction top surface is placed on top of a mechanical rehabilitation table. The table top senses tilt of the table top on a first axis with a first tilt sensor. The first tilt sensor sends first tilt signals to a controller circuit. The table top also senses tilt of the table top on a second axis with a second tilt sensor. The second tilt sensor sends second tilt signals to the controller circuit. Movements by the patient are tracked on the table top with a tracking circuit embedded in the instrumented table top. The tracking circuit sends tracking signals to the controller circuit.

In accordance with the method, the controller circuit provides the first tilt signals, the second tilt signals and the tracking signals to a communication circuit. The communication circuit transmits a signal containing the first tilt signals, the second tilt signals and the tracking signals. Of course the controller circuit can be part of the communication circuit.

In accordance with a further aspect of the method, the communication circuit wirelessly transmits the signal.

In accordance with another aspect of the present method, the patient moves his or her arm in a low-friction arm support which is atop the table top. The movements can be made in accordance with software instructions provided to the patient as previously described.

In accordance with another aspect of the present invention, arm movements of the patient are visually sensed with a camera that is located overhead of the table top. The camera can also be used to simply monitor or record a rehabilitation session.

In accordance with another aspect of the present invention, a rehabilitation kit for a patient is provided. The kit includes a instrumented table top having a low friction top and no legs, an electronic controller embedded in the table top, a first tilt sensor attached to the table top so as to sense tilt on a first axis, wherein the first tilt sensor sends a first tilt signal to the electronic controller, a second tilt sensor attached to the table top so as to sense tilt on a second axis, a tracking circuit embedded in the table top that senses movement by patients and a communication circuit attached to the table top and electrically connected to the first tilt sensor, to the second tilt sensor to the tracking circuit and to the electronic controller, wherein the communication circuit receives tilt signals from the first and second tilt sensor and tracking signals from the tracking circuit and wherein the communication circuit transmits the received signals. The kit also includes an arm support adapted to receive the arm of the patient.

This kit allows a patent to conveniently perform rehabilitation exercises at home. It also can be conveniently used at a rehabilitation center.

In accordance with further aspects of the invention, the kit can include one or more cameras. These cameras can be mounted overhead of the table top to facilitate monitoring of patient position or simple monitoring or recording of the rehabilitation process.

Additionally, in accordance with another aspect of the present invention, the kit can include software operable on a computer to provide instructions in using the table top and the arm support. That software can also be provided via the internet.

While there have been shown, described and pointed out fundamental novel features of the invention as applied to preferred embodiments thereof, it will be understood that various omissions and substitutions and changes in the form and details of the methods and/or devices illustrated and in their operation may be made by those skilled in the art without departing from the spirit of the invention. It is the intention, therefore, to be limited only as indicated by the scope of the claims appended hereto.

We claim:

1. Apparatus for rehabilitating patients, comprising:
   a table top comprising top adapted to allow a patient's arm to slide on the top surface, a bottom adapted to prevent the table top from slipping while placed on other tables, a hollow section and no legs;
   an electronic controller embedded in the hollow section of the table top;
   a first tilt sensor embedded in the hollow section of the table top so as to sense tilt on a first axis, wherein the first tilt sensor sends a first tilt signal to the electronic controller;
   a second tilt sensor embedded in the hollow section of the table top so as to sense tilt on a second axis, wherein the second tilt sensor sends a second tilt signal to the electronic controller;
   a tracking circuit attached to the table top that senses movement by a patient, wherein the tracking circuit sends a tracking signal to the electronic controller;
   a power supply embedded in the hollow section of the table top; and
   a communication circuit attached to the table top and electrically connected to the electronic controller, wherein the electronic controller sends a transmission signal including the first tilt signal, the second tilt signal and the tracking signal to the communication circuit which transmits the transmission signal
   wherein the table top has layered structure, with a plurality of modular sensing elements with a U-shaped empty section facing the patient.

2. The apparatus of claim 1, wherein the communication circuit is embedded in the hollow section of the table top.

3. The apparatus of claim 1, wherein the top layer comprises laminated plastic.

4. The apparatus of claim 1, wherein the top is manufactured from the group consisting of a matrix of sensing elements.

5. The apparatus of claim 1, wherein the bottom is rubber.

6. The apparatus of claim 1, wherein the communication circuit is wireless.

7. The apparatus of claim 1, further comprising a non-contact charging dock connected to the power supply.

8. The apparatus of claim 7, wherein the power supply is one or more batteries.

9. The apparatus of claim 1, comprising a supporting flat underside frame attached to the table top via a hinge, a handle and a manual tilt structure.

10. Apparatus for rehabilitating patients, comprising:
    a table top comprising a top adapted to allow a patient's arm to slide on the top surface, a bottom adapted to prevent the table top from slipping while placed on other tables, a hollow section and no legs;
    an electronic controller embedded in the hollow section of the table top;
    a first tilt sensor embedded in the hollow section of the table top so as to sense tilt on a first axis, wherein the first tilt sensor sends a first tilt signal to the electronic controller;
    a second tilt sensor embedded in the hollow section of the table top so as to sense tilt on a second axis, wherein the second tilt sensor sends a second tilt signal to the electronic controller;
    a tracking circuit attached to the table top that senses movement by a patient, wherein the tracking circuit sends a tracking signal to the electronic controller;
    a power supply embedded in the hollow section of the table top;
    a communication circuit attached to the table top and electronically connected to the electronic controller, wherein the electronic controller sends a transmission signal including the first tilt signal, the second tilt signal and the tracking signal to the communication circuit which transmits the transmission signal; and
    an arm support adapted to receive an arm of the patient, the arm support comprising a detachable memory foam rubber attached to a base, the detachable memory foam rubber comprising a polytetrafluoroethylene (PTFE) cover and a bottom coded to identify the patient.

11. Apparatus for rehabilitating patients, comprising:
    a table top comprising a top adapted to allow a patient's arm to slide on the top surface, a bottom adapted to prevent the table top from slipping while placed on other tables, a hollow section and no legs;

an electronic controller embedded in the hollow section of the table top;

a first tilt sensor embedded in the hollow section of the table top so as to sense tilt on a first axis, wherein the first tilt sensor sends a first tilt signal to the electronic controller;

a second tilt sensor embedded in the hollow section of the table top so as to sense tilt on a second axis, wherein the second tilt sensor sends a second tilt signal to the electronic controller;

a tracking circuit attached to the table top that senses movement by a patient, wherein the tracking circuit sends a tracking signal to the electronic controller;

a power supply embedded in the hollow section of the table top;

a communication circuit attacked to the table top and electrically connected to the electronic controller, wherein the electronic controller sends a transmission signal including the first tilt signal, the second tilt signal and the tracking signal to the communication circuit which transmits the transmission signal; and an arm support with a memory foam pad covered by a polytetrafluoroethylene (PTFE) surface and having a patient ID code and further comprising hook and loop elements spaced such to allow use of wrist weights.

* * * * *